(12) United States Patent
Sutika

(10) Patent No.: US 11,471,203 B2
(45) Date of Patent: Oct. 18, 2022

(54) APPARATUS, SYSTEM AND METHOD FOR FUSION OF BONE

(71) Applicant: SIJ Surgical, LLC, Raleigh, NC (US)

(72) Inventor: Brad Sutika, Raleigh, NC (US)

(73) Assignee: SIJ Surgical, LLC., Raleigh, NC (US)

( * ) Notice: Subject to any disclaimer, the term of this patent is extended or adjusted under 35 U.S.C. 154(b) by 126 days.

(21) Appl. No.: 16/283,278

(22) Filed: Feb. 22, 2019

(65) Prior Publication Data

US 2019/0262048 A1    Aug. 29, 2019

Related U.S. Application Data

(60) Provisional application No. 62/634,462, filed on Feb. 23, 2018.

(51) Int. Cl.
*A61B 17/86*      (2006.01)
*A61B 17/70*      (2006.01)

(52) U.S. Cl.
CPC ........ *A61B 17/8625* (2013.01); *A61B 17/864* (2013.01); *A61B 17/8635* (2013.01); *A61B 17/7055* (2013.01)

(58) Field of Classification Search
CPC .............. A61B 17/8625; A61B 17/864; A61B 17/8635; A61B 17/7055
See application file for complete search history.

(56) References Cited

U.S. PATENT DOCUMENTS

| | | | |
|---|---|---|---|
| 5,334,204 A | 8/1994 | Clewe et al. | |
| 6,517,542 B1 | 2/2003 | Papay et al. | |
| 8,029,283 B2 * | 10/2011 | Schwarz | A61C 8/0012 433/173 |
| 10,123,825 B2 * | 11/2018 | Whipple | A61B 17/864 |
| 10,687,877 B2 * | 6/2020 | Lavigne | A61B 17/0642 |
| 2006/0173461 A1 * | 8/2006 | Kay | A61B 17/8625 606/304 |
| 2007/0233125 A1 | 10/2007 | Wahl et al. | |
| 2008/0306554 A1 | 12/2008 | McKinley | |

(Continued)

OTHER PUBLICATIONS

Sutika, Brad; International Search Report and Written Opinion for PCT/US2019/019222, filed Feb. 22, 2019, dated May 15, 2019, 12 pgs.

(Continued)

*Primary Examiner* — Anu Ramana
(74) *Attorney, Agent, or Firm* — Rimas T Lukas

(57) ABSTRACT

A bone fusion screw comprises a hollow elongated body having a longitudinal axis extending between a proximal end and an open distal tip. The body defines an inner chamber bounded by an inner surface of the body extending between the proximal end and the distal tip. The body includes threads formed along at least a portion of the outer surface. At least one wedge-shaped tooth extends axially distally from the distal tip. The tooth comprises a cutting edge for cutting bone as the body is rotated. An intermediate fluted portion adjacent the distal tip comprises at least one flute. The flute has a first end adjacent the tooth at the distal tip for assisting removal of bone cuttings from the cutting edge and a second end intersecting the threads along the body. The body defines a plurality of apertures opening into the chamber.

34 Claims, 15 Drawing Sheets

(56) References Cited

U.S. PATENT DOCUMENTS

| | | | |
|---|---|---|---|
| 2011/0060373 A1* | 3/2011 | Russell | A61B 17/8057 |
| | | | 606/304 |
| 2011/0137252 A1* | 6/2011 | Oster | A61B 17/3415 |
| | | | 604/158 |
| 2011/0137352 A1 | 6/2011 | Matthis et al. | |
| 2011/0213426 A1* | 9/2011 | Yedlicka | A61B 17/8635 |
| | | | 606/309 |
| 2012/0330361 A1* | 12/2012 | Gepstein | A61L 31/126 |
| | | | 606/254 |
| 2013/0072984 A1 | 3/2013 | Robinson | |
| 2014/0243912 A1* | 8/2014 | Mobasser | A61B 17/863 |
| | | | 606/311 |
| 2016/0310187 A1 | 10/2016 | Leibinger et al. | |
| 2017/0224393 A1 | 8/2017 | Lavigne et al. | |

OTHER PUBLICATIONS

Sutika, Brad; International Preliminary Report on Patentability for PCT/US2019/019222, filed Feb. 22, 2019, dated Sep. 3, 2020, 11 pgs.

\* cited by examiner

APPARATUS, SYSTEM AND METHOD FOR FUSION OF BONE

BACKGROUND

An apparatus, system and method relating to surgical fasteners and instruments for musculoskeletal surgical procedures and, in particular, screws, tools and methods for use in connection with bone fusion, such as in a sacroiliac joint.

Bone fusion is used when it is desired to hold bones in a fixed position with respect to each other. One circumstance where it is desirable to hold bones together is after a fracture. A screw or other fixation device may be inserted into two separate bone pieces. The screw holds the bones in a stationary position until bone grows there between to fuse the bone pieces together.

Another circumstance where it is desired to hold bones together is when performing a sacroiliac fusion. The sacroiliac (SI) joint is formed by the meeting of the sacrum at the base of the spine and the ilium at the upper part of the pelvis. The sacroiliac joint spans between the sacrum bone and the ilium bone and has a rotation of one to two degrees. The SI joint is subject to degenerative disease and instability or can be damaged, resulting in lower back and leg pain attributed to symptomatic sacroiliac dysfunction or instability.

A treatment for indications such as pain at the sacroiliac joint includes fusing together the sacrum and the ilium. Some of the problems associated with joint fusion or sacral fixation procedures are the difficult anatomy of the area, poor bone quality sometimes found in the sacrum, and the large lumbosacral loads and cantilever pullout forces applied across the region. The bone quality of the sacrum may be poor even in patients who do not have weak bone.

Screws and screws with plates are used for sacroiliac joint fusion. Screws or screw-type implants tend to be susceptible to rotation and loosening, especially in joints that are subjected to torsional forces, such as the SI joint. Also, excessive movement of the implant after implantation may result in the failure of the implant to incorporate and fuse with the bone, which can result in the need to remove and replace the failed implant.

For the foregoing reasons there is a need for improved apparatus, systems and methods for correcting symptomatic sacroiliac dysfunction or instability. The apparatus and system should include sacroiliac joint fusion or fixation fasteners, such as screws, and associated instruments and procedures, for immobilizing the SI joint. Ideally, the screw should resist rotation and can be implanted using a minimally invasive procedure. Ideally, the screw may also be used in conjunction with bone fractures for maintaining adjacent bone pieces in a stationary position with respect to each other as part of a bone fusion.

SUMMARY

A bone fusion screw comprises a hollow elongated body having a longitudinal axis extending between a proximal end and an open distal tip. The body defines an inner chamber bounded by an inner surface of the body and extending between the proximal end and the distal tip. The body includes threads formed along at least a portion of the outer surface. At least one wedge-shaped tooth extends axially distally from the distal tip. The at least one tooth comprises a cutting edge for cutting bone to form a bore in the bone as the body is rotated. An intermediate fluted portion is adjacent the distal tip. The fluted portion comprises at least one flute having a first end adjacent the tooth at the distal tip for assisting removal of bone cuttings from the cutting edge and a second end intersecting the threads along the body. The body defines a plurality of apertures opening into the chamber.

In one aspect, a transverse cross-section of the chamber is substantially circular. In another, the threads extend substantially between the proximal end and the distal end of the outer surface of the body.

In a further aspect, the at least one tooth tapers radially outwardly from the inner surface of the body to the cutting edge for directing bone into the chamber upon rotation of the body in bone. The at least one tooth may comprise two cutting edges.

In another aspect, the at least one flute extends along the outer surface of the body in a direction substantially parallel to the longitudinal axis. The flute may extend along a helical path from the first end to the second end. The he threads on the outer surface of the body are oriented at a pitch that is different from the pitch of the flute. In an embodiment, the fluted portion comprises two pairs of opposed flutes.

In still another aspect, the apertures are adapted to receive bone growth material. In one embodiment, the apertures are elliptical and each of the apertures is between the threads. An even number of opposed apertures may be formed at a plurality of spaced axial locations along the body.

The bone fusion screw can further comprise a head integral with the proximal end of the body. In one aspect, the head has an outer diameter that is greater than an outer diameter of the threads and may comprise structure configured for receiving a driver for rotating the body. In this aspect, the head defines a channel opening into the chamber in the body and the channel may be coaxial with the chamber forming a cannula through the bone fusion screw. The surface of the head defining the channel can comprise threads adapted to be threadably coupled to a threaded driver to secure the driver within the channel of the head.

In a further aspect, the outer surface of the body is roughened to assist in osteointegration.

A method for securing at least a first bone and a second bone to each other is also provided. The bone securing method comprises the steps of forming an aperture that extends between the first bone and the second bone and providing a bone fusion screw. The bone fusion screw comprises a hollow elongated body having a longitudinal axis extending between a proximal end and an open distal tip. The body defines an inner chamber bounded by an inner surface of the body and extending between the proximal end and the distal tip. The body also includes threads formed along at least a portion of the outer surface. At least one wedge-shaped tooth extends axially distally from the distal tip. The at least one tooth comprising a cutting edge for cutting bone to form a bore as the body is rotated. An intermediate fluted portion is adjacent the distal tip. The fluted portion comprises at least one flute having a first end adjacent the tooth at the distal tip for assisting removal of bone cuttings from said cutting edge and a second end intersecting the threads along the body. The body defines a plurality of apertures opening into the chamber. In the present method, the next step is positioning a driver in engagement with the body, and rotating the driver and engaged body to cause the bone fusion screw to be screwed into the first bone and the second bone to a depth such that the threads are engaged in both the first bone and the second bone. A portion of the bone connected to the surrounding bone extends into the chamber through the open distal end.

The body is positioned for bone growth through the plurality of apertures and into the chamber to fuse the first bone to the second bone.

In another embodiment, the bone securing method further comprises the step of placing a fusion-promoting material in the chamber of the body. The fusion-promoting material is allograft bone, cortical bone, tricalcium phosphates, hydroxyapatite, BIOCRYL™ hydroxyapatite, bioglass, polymer composites, bone-derived substances, demineralized bone matrix, mineralizing proteins, ossifying proteins, bone morphogenetic proteins, genes coding for the production of bone and combinations thereof.

In one aspect, the step of providing the bone fusion screw further comprises proving a bone fusion screw including a head portion integral with the body at the proximal end, wherein the head portion comprises structure configured for receiving a driver for rotating the body, and the step of positioning the driver in engagement with the body comprises positioning the driver in engagement with the driver receiving structure in the head.

In another aspect, the bone securing method further comprises the step of placing a washer around the body shaft before implanting the screw.

A system for fixation of bone is provided, comprising a bone fusion screw and a driver having a distal end that is engageable with the head for rotating the bone fusion screw. The bone fusion screw comprises a hollow elongated body having a longitudinal axis extending between a proximal end and an open distal tip. The body defines an inner chamber bounded by an inner surface of the body and extending between the proximal end and the distal tip. The body includes threads formed along at least a portion of the outer surface. At least one wedge-shaped tooth extends axially distally from the distal tip, the at least one tooth comprising a cutting edge for cutting bone to form a bore as the body is rotated. An intermediate fluted portion adjacent the distal tip comprises at least one flute having a first end adjacent the tooth at the distal tip for assisting removal of bone cuttings from said cutting edge and a second end intersecting the threads along the body. The body defines a plurality of apertures opening into the chamber;

In one aspect, the driver comprises a handle portion and a distal driving end portion that extends from the handle portion, and the distal end portion may conform to at least a portion of a channel formed in the body.

In one embodiment, a head has internal threads within a channel, and at least a portion of the distal end portion of the driver has an external threaded surface configured to be threadably coupled with the internal threads to secure the driver within the channel.

In another embodiment, the bone fixation system further comprises a washer configured to be disposed around the body before implanting the screw. The washer may include axial teeth extending from a distal surface.

BRIEF DESCRIPTION OF THE DRAWINGS

For a more complete understanding of the apparatus, method and system for fusion of bone, reference should now be had to the embodiments shown in the accompanying drawings and described below. In the drawings.

DETAILED DESCRIPTION

Figure 1A:
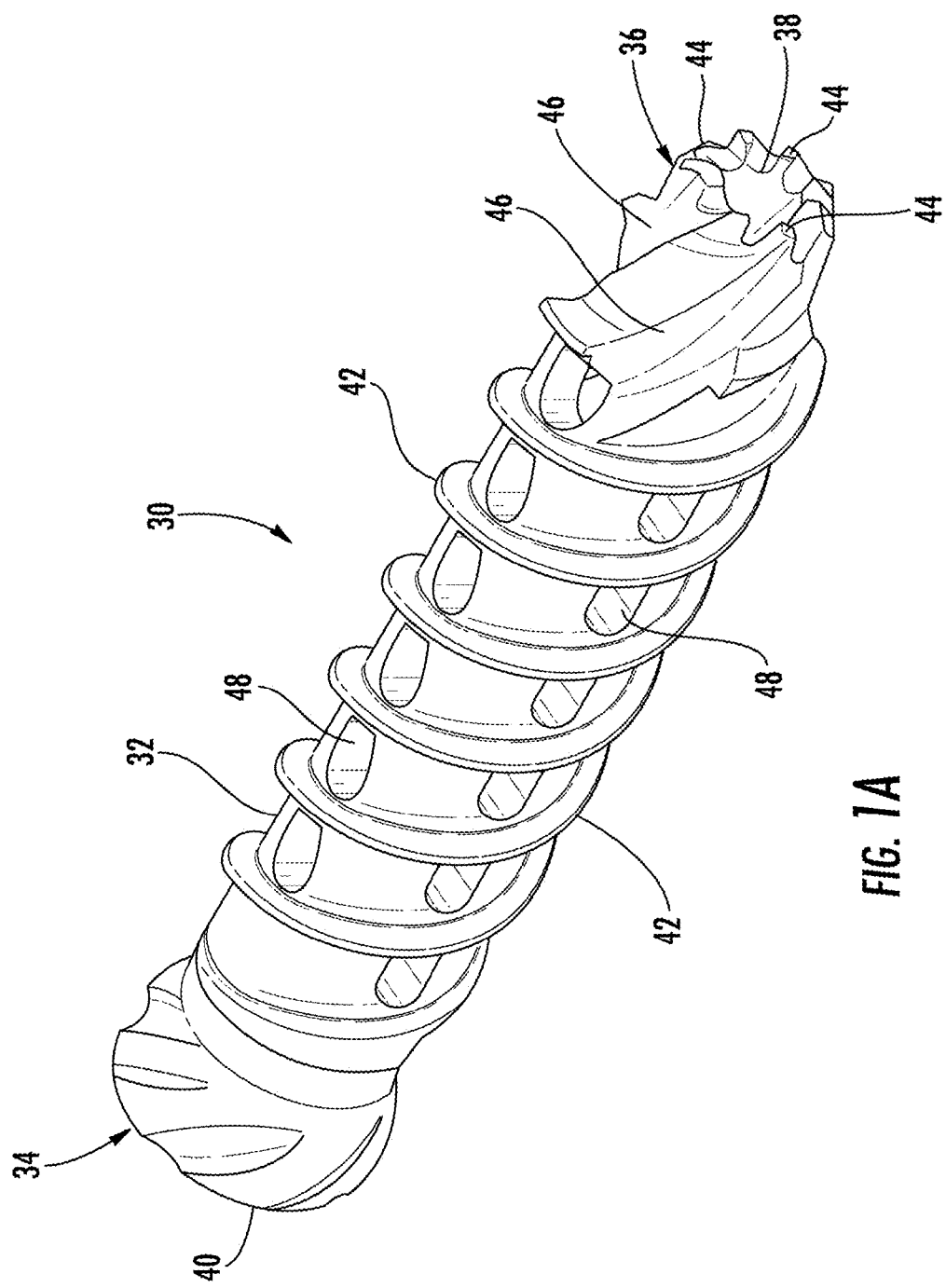
FIG. 1A is a perspective view from a distal end of an embodiment of a screw for use in a bone fusion procedure.
Figure 1B:
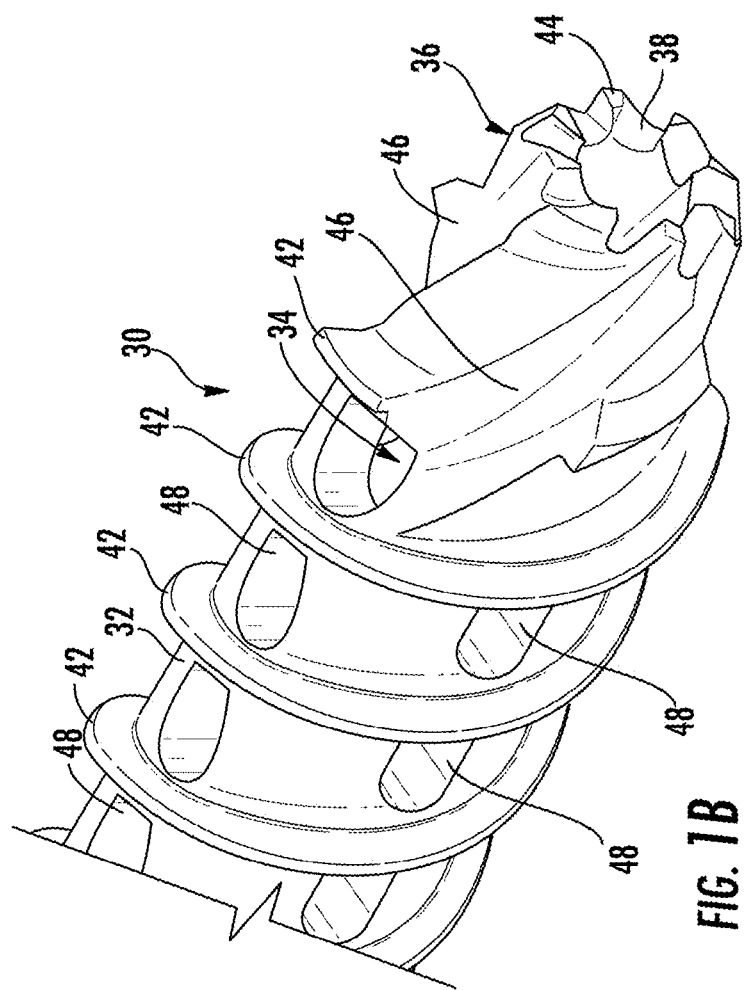
FIG. 1B is a close up perspective view of the distal end of the screw as shown in FIG. 1A.
Figure 2:
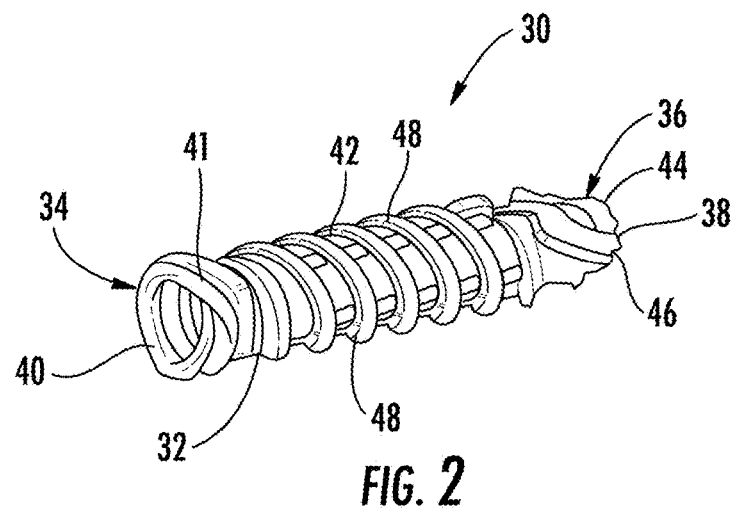
FIG. 2 is a perspective view from a proximal end of the screw as shown in FIG. 1A.
Figure 3:
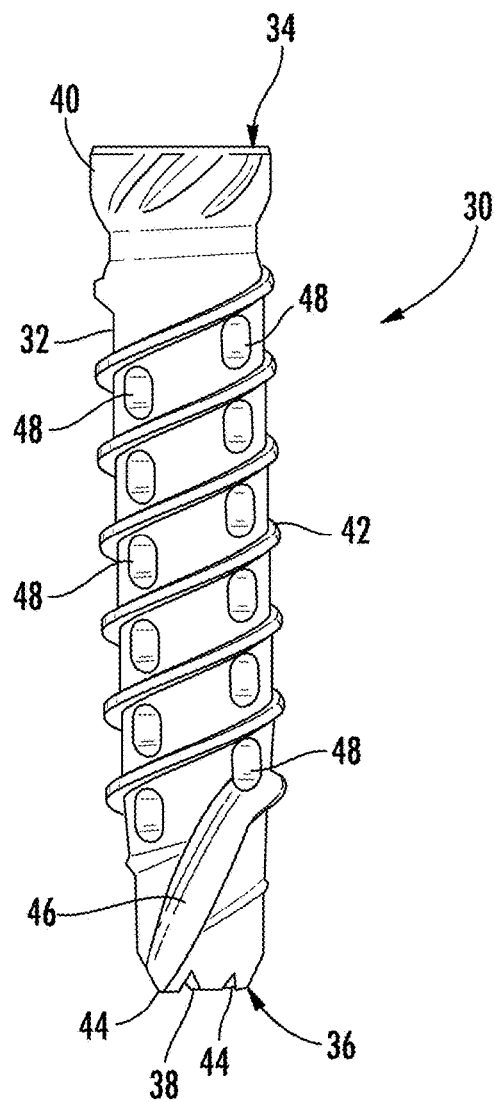
FIG. 3 is a side elevation view of the screw as shown in FIG. 1A.
Figure 4:
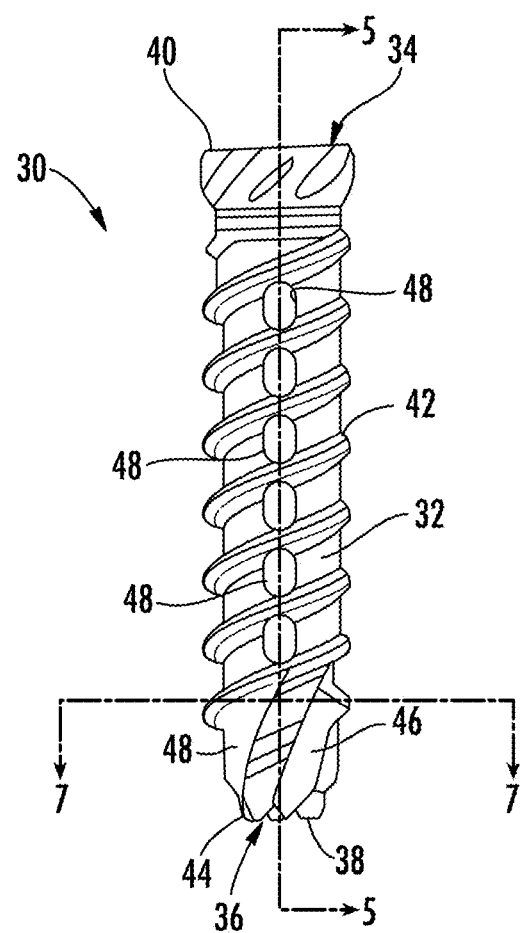
FIG. 4 is a side elevation view of the screw as shown in FIG. 3 with the screw slightly rotated along a central longitudinal axis relative to FIG. 3.

Certain terminology is used herein for convenience only and is not to be taken as a limiting. For example, words such as "upper," "lower," "left," "right," "horizontal," "vertical," "upward," "downward," "top" and "bottom" merely describe the configurations shown in the drawings. Indeed, the components may be oriented in any direction and the terminology, therefore, should be understood as encompassing such variations unless specified otherwise. The words "interior" and "exterior" refer to directions toward and away from, respectively, the geometric center of the core and designated parts thereof. The terminology includes the words specifically, derivatives thereof and words of similar import.

Referring now to the drawings, wherein like reference numerals designate corresponding or similar elements throughout the several views, an embodiment of a bone fusion screw for use in sacroiliac joint fusion is shown and generally designated at 30. Referring to FIGS. 1A-5, the bone fusion screw 30 comprises an elongated cylindrical hollow shank or shaft 32 having a first proximal end 34 and a second distal end 36 with a tip 38. A head 40 is integral with the proximal end 34 of the shaft 32. The head 40 has a diameter larger than the diameter of the shaft 32. The tip 38 carries a series of axially extending wedge-shaped teeth 44. A plurality of helical bone cutting flutes 46 extend along a portion of the distal end 36 of the shaft 32 adjacent to the tip 38 and terminating at the teeth 44.

The hollow shaft 32 defines an interior chamber 33 (FIG. 5) extending from the proximal end 34 of the shaft 32 to the tip 38. The inner surface of the walls of the chamber 33 in the shaft 32 are smooth and generally circular in transverse cross-section. The outer surface of the shaft 32 has threads 42 extending between the head 40 of the screw 30 and the tip 38. The threads 42 are configured to engage bone. The shaft 32 defines a plurality of fenestrations 48 between the threads 42 and opening into the chamber 33 inside the shaft 32. In the embodiment shown in the drawings, four fenestrations 48 are equally spaced around the circumference of the shaft 32 at a plurality of axial locations along the length of the shaft 32. In this arrangement, the fenestrations 48 in each of two pairs of fenestrations 48 at each axial location are aligned for forming a window through the body. In addition, each fenestration 48 is axially aligned with the immediately proximal and distal fenestrations 48 forming a linear arrangement of fenestrations 48 from the proximal to distal end of the screw 30. Preferably, the fenestrations 48 along the shaft define elongated elliptical slots. The fenestrations 48 can also define other geometric shapes, including curvilinear shapes, such as oval or circular, and can be of different sizes. It is understood that the fenestrations 48 can alternatively be rectilinear in shape, such as triangular, square, rectangular, and the like. The fenestrations 48 promote bony ingrowth into the shaft 32 and allow the introduction of bone graft material into the chamber 33 internally of the shaft 32. Autograft cut bone fragments may be directed into the "window" openings formed by the fenestrations 48 to enhance new bone growth and rapid fusion of bone and the screw 30.

The bone fusion screw 30 can be fabricated from metal or metal alloy, such as titanium or titanium alloys, steel (e.g. stainless steel), steel alloys. Other non-metallic material including ceramics or polymers can be used. These materials are generally nontoxic, bio-compatible, strong and non-corrosive. Other materials that have these properties may also be used.

The shaft 32 of the bone fusion screw 30 can have any length suitable for a bone fusion application. Embodiments of the screw 30 can, for example, have shaft lengths from 30 mm to 80 mm, preferably in 5 mm increments. The shaft 32 may have a substantially constant diameter along its length, or the diameter of the shaft 32 may vary and include a tapered distal end 36. For example, the diameter of the shaft 32 may be widest at a location on the shaft 32 adjacent to the head 40 of the bone fusion screw 30. In some embodiments of the screw 30, the diameter of the head 40 is about the same diameter as the shaft 32, although other embodiments of the screw 30 may have heads with larger or smaller diameters.

The threads 42 of the screw 30 may start at or near the head 40 and extend to the tip 38 at the distal end 36 of the shaft 32. A function of the threads 42 of the screw 30 is to engage bone when implanted, for example, in the ilium and sacrum of the sacroiliac joint. The threads 42 may have a constant thread depth along the length of the threaded portion of the shaft 32. Alternatively, the depth of the threads 42 may vary. For example, the depth of the threads 42 may be greater along a proximal portion of the screw 30 adjacent to the head 40. The threads 42 depth may then be tapered such that the thread depth decreases near the tip 38 of the screw 30. The larger thread depth proximate the head 40 may allow the screw 30 to provide better purchase in soft bone tissue. In one embodiment, the diameter of the shaft can be about 10 mm and the depth of the threads 42 can be about 3 mm. Other embodiments of the bone fusion screw 30 may have larger or smaller diameters.

Thread 42 pitch ranges and it is understood the threads 42 of the screw 30 can have larger and smaller thread pitch.

Figure 9:
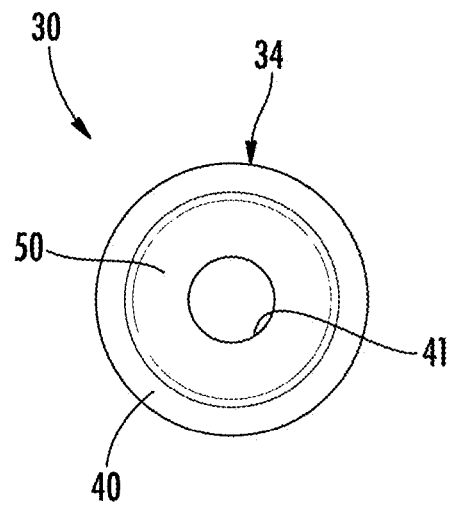
FIG. 9 is a top plan view of the screw as shown in FIG. 1A.
Figure 10:
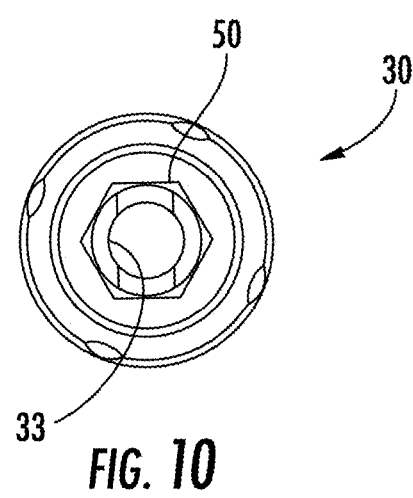
FIG. 10 is a bottom plan view of the screw as shown in FIG. 1A.
Figure 11:
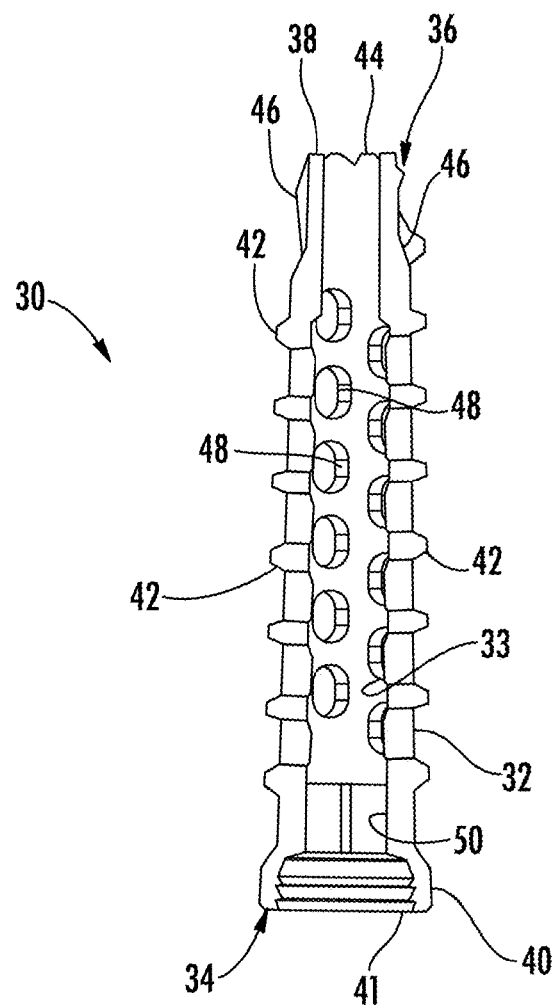
FIG. 11 is a longitudinal cross-section view of the screw taken along line 11-11 of FIG. 3.

The head 40 has a central aperture 41 opening into the chamber 33 inside of the shaft 32 (FIGS. 9-11). The center of the aperture 41 is coaxial with a central longitudinal axis of the screw 30 such that the screw has a continuous cannula extending between the proximal end 34 and the distal end 36 of the shaft 32. The bone fusion screw 30 can therefore be cannulated via the aperture 41 in the head 40 for passing a guide wire (not shown) through the elongated shaft 32. The guide wire can be used during an implant procedure as a drill guide or alignment guide to achieve proper trajectory and alignment of the bone fusion screw 30. Some embodiments of the screw 30 can, for example, have a cannula of about 2.5 mm in diameter, although other embodiments may have larger or smaller cannula diameters.

Figure 15:
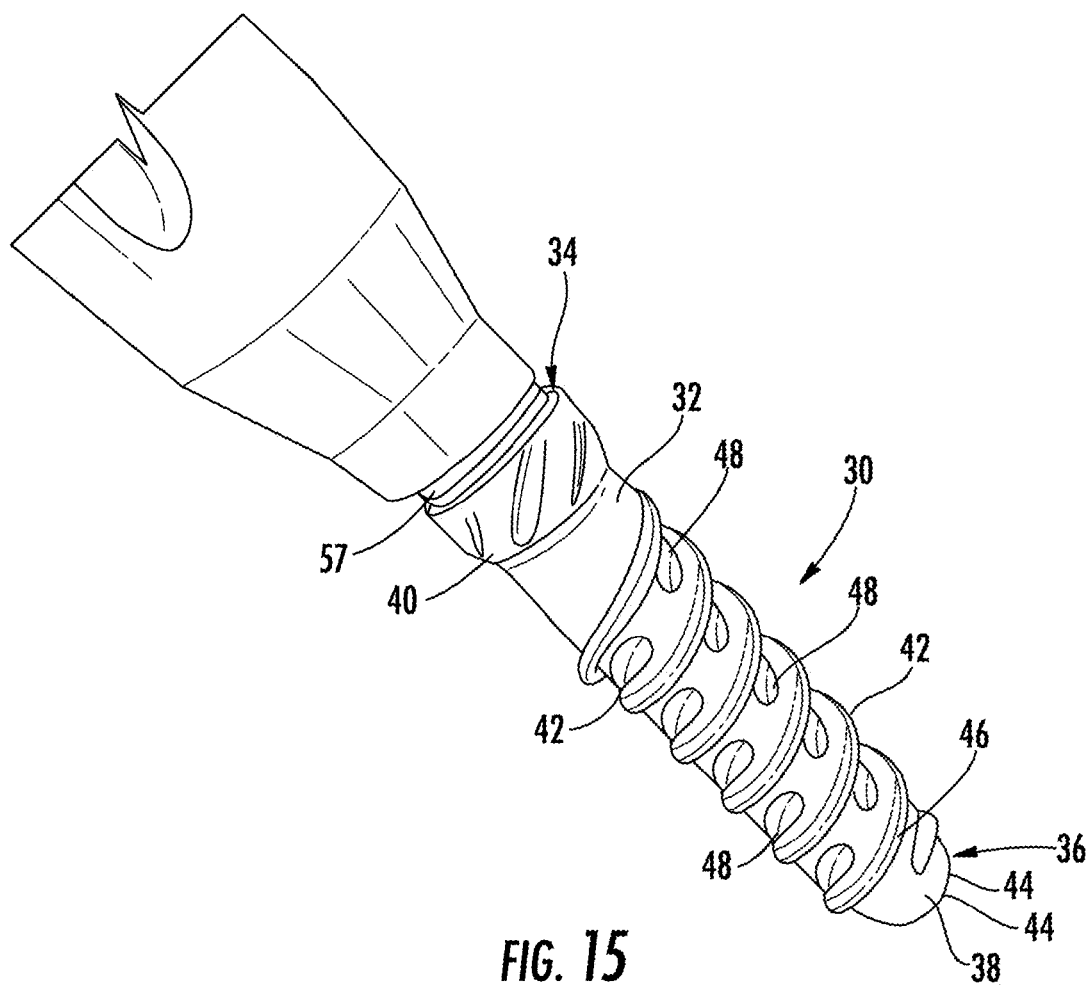
FIG. 15 is a perspective view of the screw as shown in FIG. 1A and a rotatable driver attached to head at a proximal end of the screw.

The head 40 of the screw 30 may further define a proximal cavity 50 coaxial with the aperture 41 and configured to receive an end of a torqueing tool 56, or other driver, for threading the screw 30 into the bone. As shown in FIG. 15, the cavity 50 may be internally threaded for engaging an externally threaded end or tip 57 of the driver 56 configured to be threadably coupled with the inner threads in the head 40 to secure the driver 56 within the head 40 to fix the driver to the screw 30. Other embodiments of the screw 30 may include a head 40 having other driver tool-receiving structure, such as a hex head or a hex cap.

Figure 7:
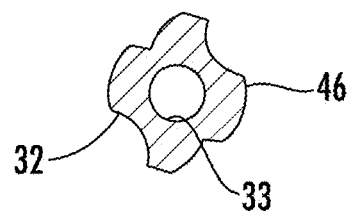
FIG. 7 is a transverse cross-section top plan view of the screw taken along line 7-7 of FIG. 4.
Figure 8:
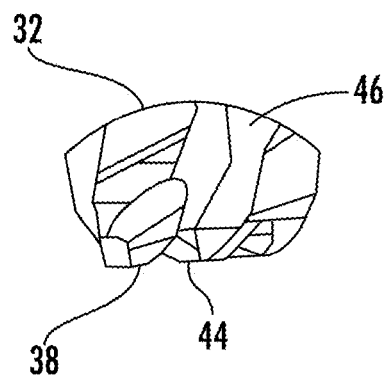
FIG. 8 is a close-up view of a distal end of the screw as shown in FIG. 4.
Figure 12:
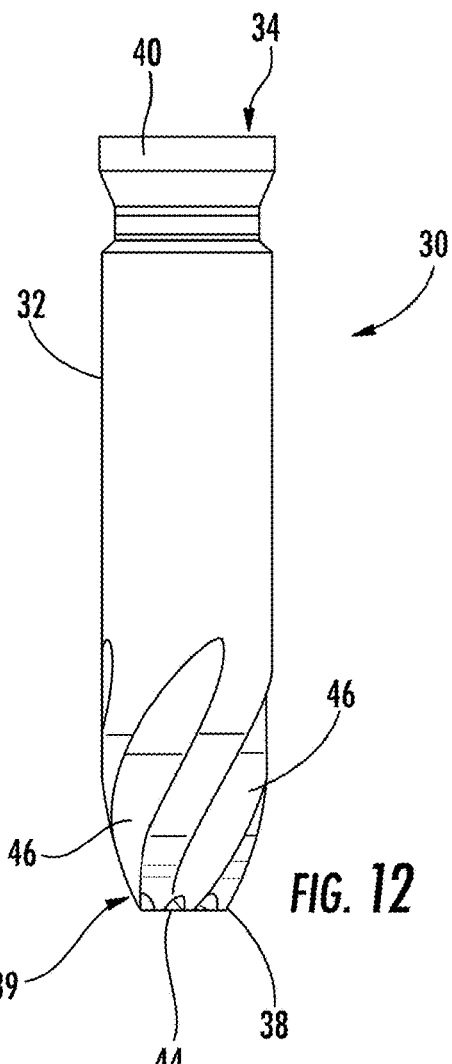
FIG. 12 is a side elevation view of the screw as shown in FIG. 3 showing only the cutting flutes for clarity.

In one embodiment of the screw, two pairs of cutting flutes 46 are provided. In the configuration shown in the drawings, each flute 46 of a pair of flutes is diametrically opposed from the other. Referring to FIGS. 7, 8 and 12, each flute 46 has a cutting edge formed from a leading end at or near the tip 38 of the screw 30 on the circumferential exterior of the tip and extending helically along an arcuate ramp in a plane parallel to the longitudinal axis of the shaft 32, terminating at or near the start of the threads 42 partially overhanging the flutes 46. The cutting edges of the flutes 46 cut bone to facilitate insertion of the screw 30.

Figure 5:
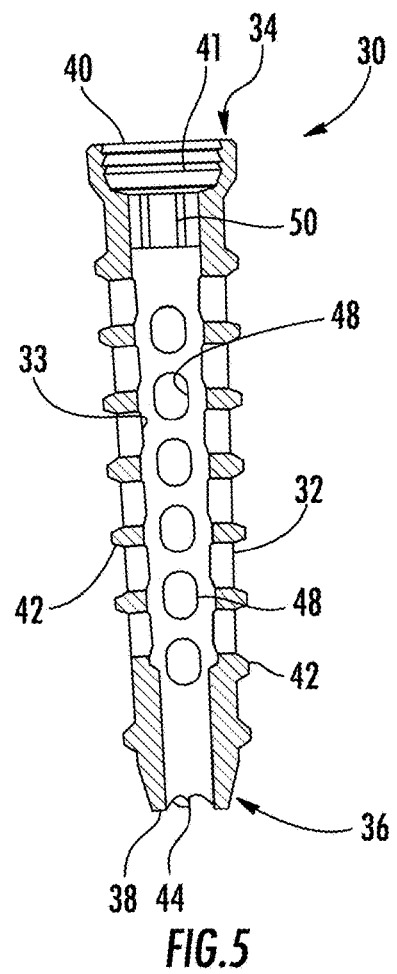
FIG. 5 is a longitudinal cross-section side elevation view of the screw taken along line 5-5 of FIG. 4.
Figure 6:
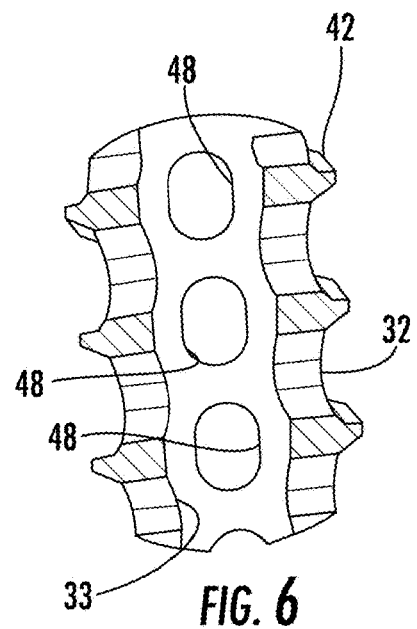
FIG. 6 is a close-up view of a portion of the screw as shown in FIG. 5 showing three fenestrations.

The wedge-shaped teeth 44 are circumferentially spaced along the distal periphery of the distal tip of the shaft 32. The teeth 44 taper from their distal cutting edges toward an inside diameter of the hollow shaft 32. The inside diameter of the chamber 33 of the shaft 32 thus narrows from the distal ends of the teeth 44 to an interior axial location at or near the start of the threads 42 (FIG. 5). The inside diameter of the chamber 33 then widens proximally of the axial location. During implantation of the screw 30 into bone, the teeth 44 are configured to engage the bone surface as the screw 30 turns to cut the bone. The teeth 44 configuration allows a live uncut bone plug, or core, of cortical cancellous bone to advance internally upwardly into the chamber 33 in the shaft 32 as the screw is driven. In this arrangement, the bone plug or core in the chamber 33 of the shaft 32 remains connected to the original surrounding bone post implantation to increase osteoconductivity.

The screw 30 can be manufactured using a variety of techniques. In one embodiment, the screw 30 can be 3-D printed using a rapid prototyping technique involving additive manufacturing. The 3-D printed screw 30 can be made of a metal, polymer, or ceramic material. For example, a metal powder such as titanium powder can be fused together to form the screw 30. Other manufacturing techniques could include cutting out the fenestrations using a laser, for example, or using electric discharge machining (EDM) to create the fenestrations. Certain features of the screw 30 could even be welded together, although a laser cut structure may be structurally stronger than a welded structure.

Figure 13:
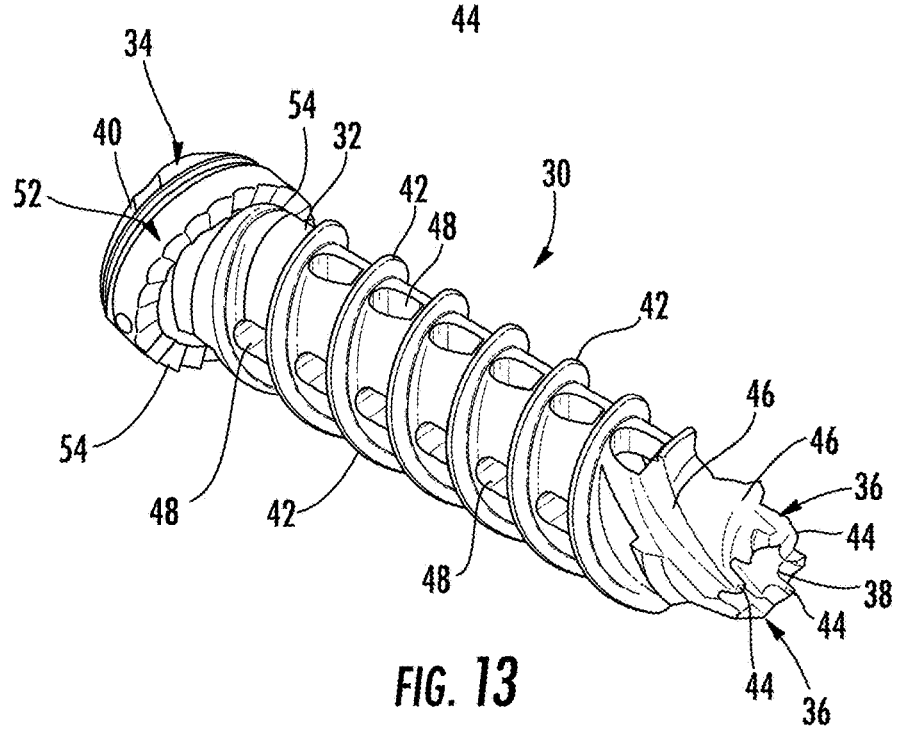
FIG. 13 is a perspective view from a distal end of the screw as shown in FIG. 1A and including a washer adjacent a head of the screw.
Figure 14:
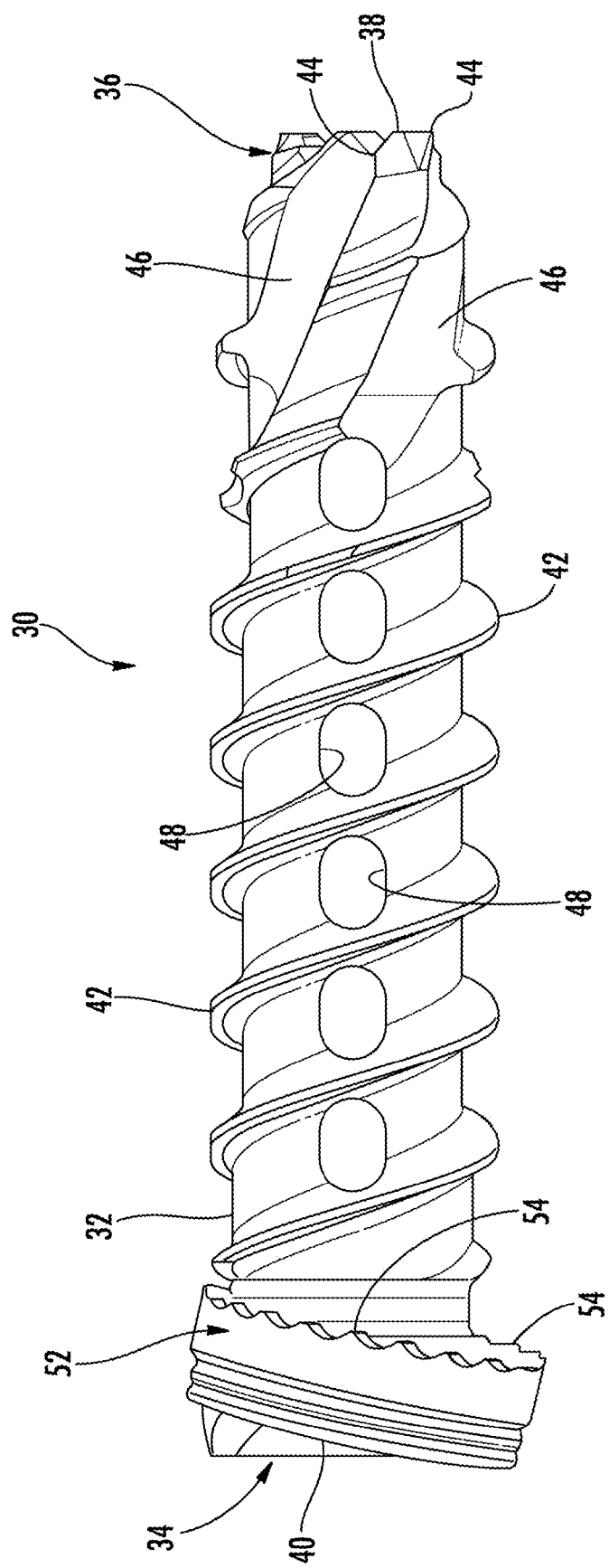
FIG. 14 is a side elevation view of the screw as shown in FIG. 13.
Figure 16:
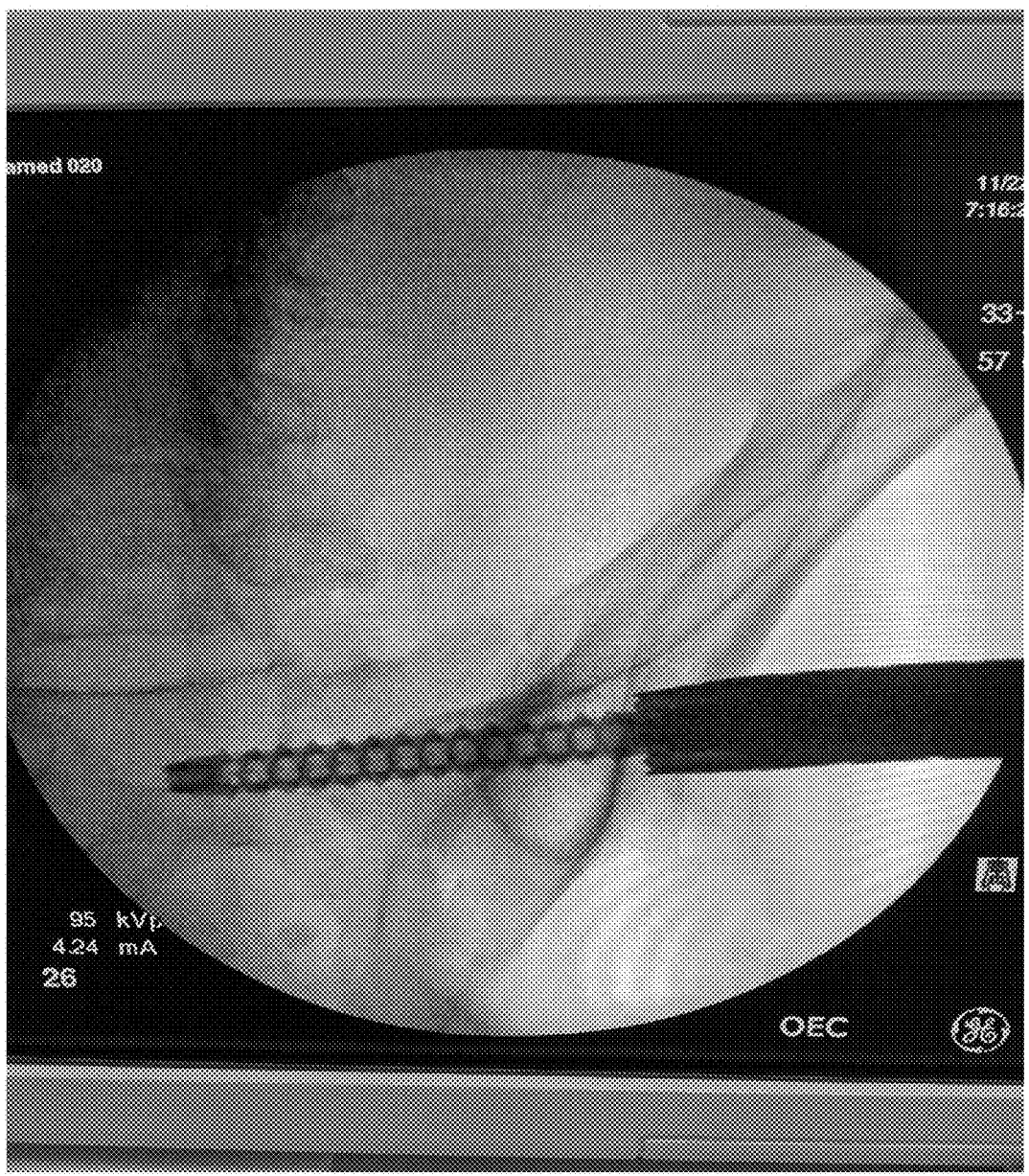
FIG. 16 is an x-ray photograph of the screw as shown in FIG. 1A implanted in a sacroiliac joint.

FIGS. 13 and 14 show a disc-shaped washer 52 configured to receive the shaft 32 of the screw 30 up to the distal surface of the head 40. The washer 52 comprises a series of axially extending wedge-shaped teeth 54 circumferentially spaced along the distal end of the washer 52. This arrangement allows the washer 52 upon insertion to occupy a space between the screw head 40 and the bone such that the teeth 54 engage the bone surface as shown in FIG. 16. In this position, the screw 30 cannot back out.

Figure 17:
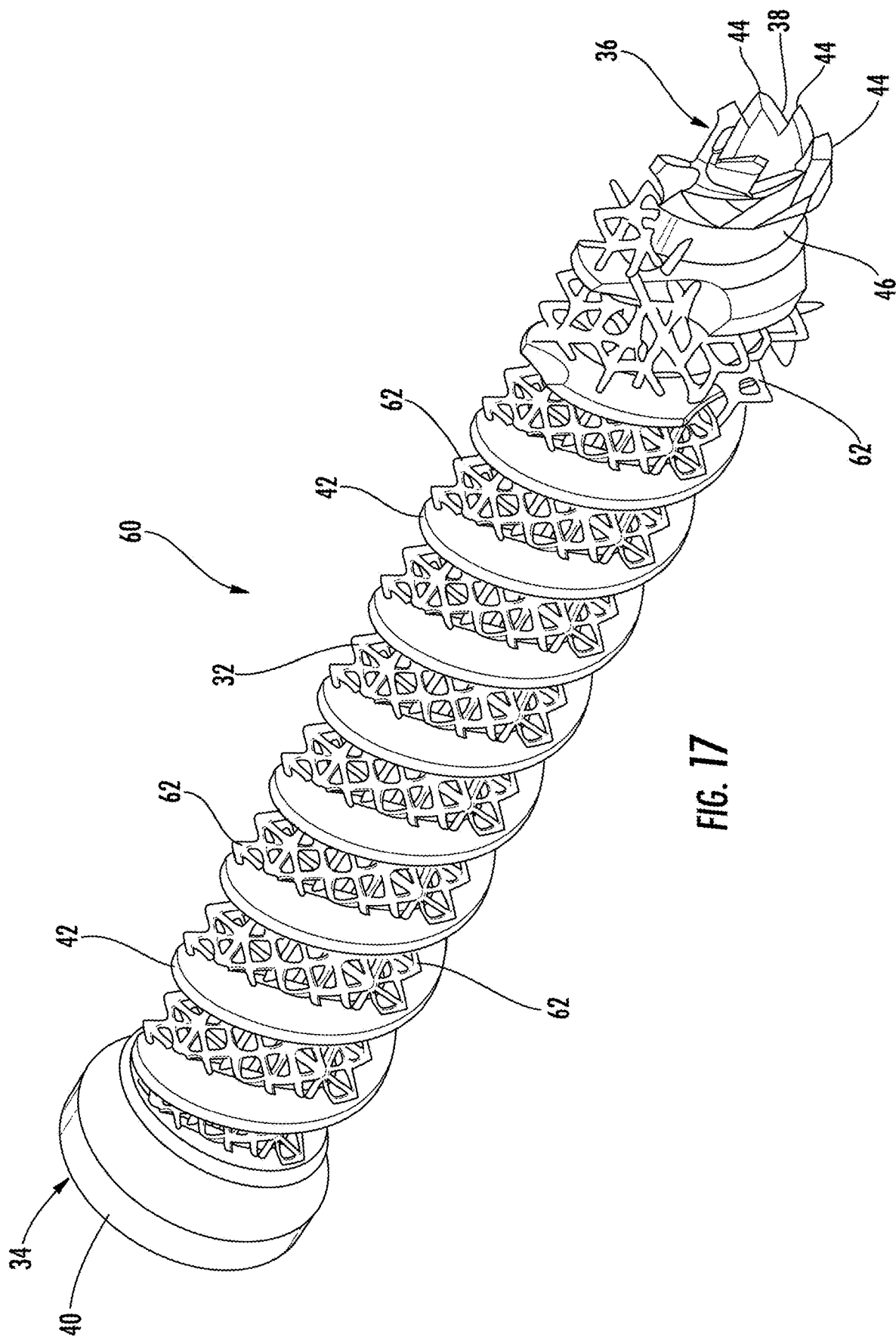
FIG. 17 is a perspective view of another embodiment of a screw for use in a sacroiliac joint.
Figure 18:
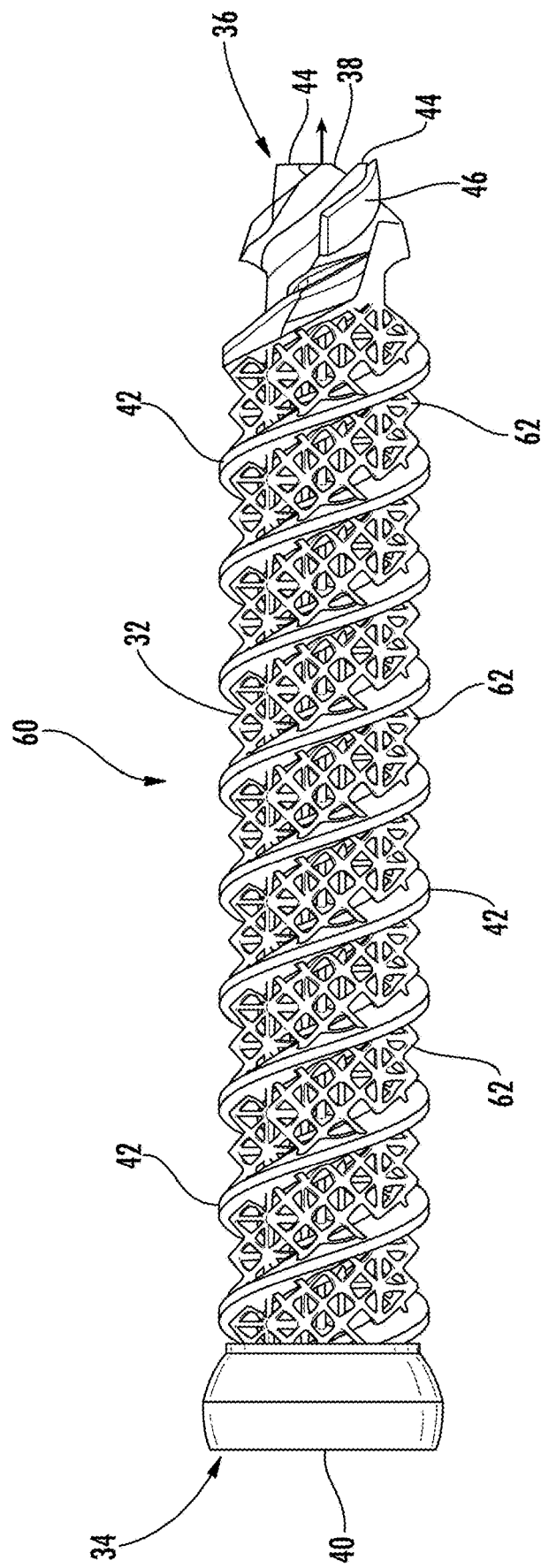
FIG. 18 is a side elevation view of the screw as shown in FIG. 17.
Figure 19:
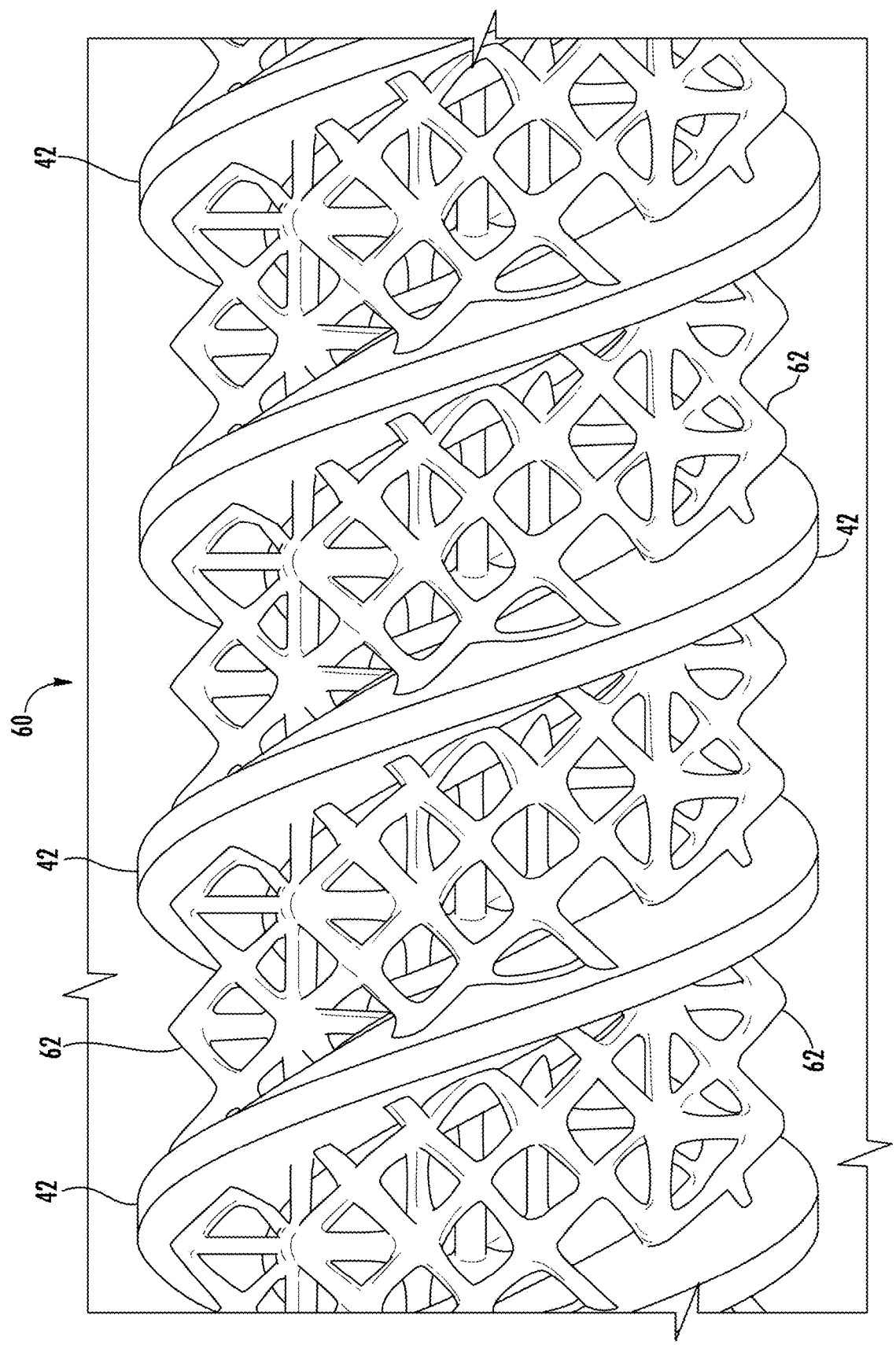
FIG. 19 is a close-up view of a portion of the screw as shown in FIG. 17.

Referring now to FIGS. 17-19, another embodiment of a bone fusion screw for use in sacroiliac joint fusion is shown and generally designated at 60. In this embodiment, of the screw 60, the outer surface 62 of the shaft 32 comprises a textured, lattice-type matrix between the threads 42. The textured matrix structure 62 of the screw 60 results in a rough surface which may function to inhibit or resist movement of the screw 60 when the screw is fixed within bone. The matrix structure provides a level of resistance to various forces that the implant will be subjected to, including compressive, tensile, shear, bending, and torsional forces. The matrix structure 62 also provides strength to the screw 60. This embodiment of the screw 60 does not have fenestrations.

The matrix structure can be a regular repeating pore shape, such as triangular, cubic, hexagonal, and the like. In one embodiment, the textured outer surface 62 provides a matrix having a pore size between about 100 to 1000 microns. The textured matrix 62 of the outer surface of the screw 60 is provided by surface finishing techniques, such as polishing or application of a metal plasma spray. Other suitable alternatives include using a laser or EDM to form the textured matrix surface.

In use, the bone fusion screw 30, 60 can be used in one application to fuse a sacroiliac joint 80 in a transiliac fixation procedure. Referring to FIG. 16, the sacroiliac joint 80 is typically approached from the side of the ilium 82. Using a tool such as a drill (not shown), a pilot hole is first bored through the ilium 82 and into the sacrum 84 at the location to be fused. In one alternative, a pin (not shown) can first be inserted through the ilium 82 and into the sacrum 84 to define a path through the SI joint 80 at the desired fusion site. The surgeon can then use the pin as a guide path for the drill when boring a pilot hole through the ilium 82 and the sacrum 84 at the fusion site. A decortication procedure can optionally be performed at the fusion site to remove tissue from the ilium 82 or sacrum 84 in the area of the SI joint 80 to be fused by using a reamer or other suitable tool inserted into the pilot hole. Bone graft material can optionally be inserted into the area.

An appropriate length screw 30, 60 is then selected. The screw 30, 60 is then implanted into the SI joint 80 by using a driver to thread the screw 30, 60 into the pilot hole. The teeth 44 and the cutting edges of the flutes 46 cut into the bone upon screw 30, 60 rotation during implantation. The step of threading of the screw 30, 60 directs a portion of bone still a part of the surrounding remainder of the bone into the chamber 33 of the shaft 32 to enhance subsequent fusion. As shown in FIG. 16, when fully implanted the threaded portion of the screw 30, 60 extends through and engages the ilium 82 and the sacrum 84. Because the threaded portion of the screw 30, 60 is in purchase with the bone and the head 40 engages the ilium 82, the screw 30, 60 provides compression of the SI joint as the ilium 82 and sacrum 84 are urged together by the screw 30, 60. The optional washer 52 located on the shaft 32 between the head 40 and the ilium 82 can further prevent the screw 30, 60 from backing out.

Bone graft material, for example autograft bone material collected from the patient during the boring step or the decortication step, can be inserted at the fusion site after implantation into the chamber 33 of the shaft 32 via the aperture 41 in the head 40 of the screw 30, 60. Allograft bone or other biocompatible and bioactive materials may also be added to the screw 30, 60 after implantation or during the surgical procedure to enhance new bone growth. Alternatively, the screw can be packed with graft material prior to implantation. Some of this material will be pushed out of the plurality of fenestrations 48 as the screw 30, 60 is advanced to aid in fusion around and into the screw. In addition, new bone growth through the fenestrations 48 provides rapid fusion of the screw 30, 60.

The procedure shown herein illustrates insertion of the screw 30, 60 across the SI joint 80 using a lateral approach that goes laterally through the ilium 82 across the SI Joint and into the sacrum 84. The screw 30, 60 can also be used across the SI joint 80 using a postero-lateral approach entering from the posterior iliac spine of the ilium 82, angling through the SI joint, and terminating in the sacral alae.

It is understood that the apparatus, methods and associated devices described herein may be used to perform various bone fusions of any two bone segments, such as two bones that form a joint or two pieces of bone resulting from a fracture. For example, the bone fusion screw 30, 60 may be used in other pelvic or lumbo-pelvic fusions or stabilization procedures or spinal fixation to correct problems in the lumbar and thoracic portions of the spine.

Although a bone fusion screw and associated delivery tools and methods is shown and described in considerable detail with respect to only a few exemplary embodiments thereof, it should be understood by those skilled in the art that we do not intend to limit the apparatus and methods to the embodiments since various modifications, omissions and additions may be made to the disclosed embodiments without materially departing from the novel teachings and advantages, particularly in light of the foregoing teachings. Accordingly, we intend to cover all such modifications, omission, additions and equivalents as may be included within the spirit and scope of the bone fusion screw and methods as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

That which is claimed is:

1. A bone fusion screw, comprising:
   a hollow elongated body having a longitudinal axis extending between a proximal end and an open distal tip, the body defining an inner chamber bounded by an inner surface of the body and extending between the proximal end and the distal tip, the body including threads formed along at least a portion of the outer surface;
   a head integral with the proximal end of the body; wherein the head defines a channel opening into the chamber in the body; and wherein the surface of the head defining the channel comprises threads adapted to be threadably coupled to a threaded driver to secure the driver within the channel of the head;

at least one wedge-shaped tooth extending axially distally from the distal tip, the at least one tooth comprising a cutting edge for cutting bone to form a bore in the bone as the body is rotated; and an intermediate fluted portion adjacent the distal tip and intersecting the threads along the body, the fluted portion comprising at least one flute having a first end integral with the tooth at the distal tip for assisting removal of bone cuttings from the cutting edge;

wherein the body defines a plurality of apertures between the threads and opening into the chamber; and wherein pairs of opposed apertures are located at a plurality of spaced axial locations along the body for providing a see: through opening through the body at each of the spaced axial locations.

2. The bone fusion screw as recited in claim 1, wherein a transverse cross-section of the chamber is substantially circular.

3. The bone fusion screw as recited in claim 1, wherein the threads extend substantially between the proximal end and the distal end of the outer surface of the body.

4. The bone fusion screw as recited in claim 1, wherein the at least one tooth tapers radially outwardly from the inner surface of the body to the cutting edge for directing bone into the chamber upon rotation of the body in bone.

5. The bone fusion screw as recited in claim 1, wherein the at least one tooth comprises two cutting edges.

6. The bone fusion screw as recited in claim 1, wherein the at least one flute extends along the outer surface of the body in a direction substantially parallel to the longitudinal axis.

7. The bone fusion screw as recited in claim 1, wherein the flute extends along a helical path from the first end to the second end.

8. The bone fusion screw as recited in claim 7, wherein the threads on the outer surface of the body are oriented at a pitch that is different from the pitch of the helical path of the flute.

9. The bone fusion screw as recited in claim 1, wherein the fluted portion comprises two pairs of opposed flutes.

10. The bone fusion screw as recited in claim 1, wherein the apertures are adapted to receive bone growth material.

11. The bone fusion screw as recited in claim 1, wherein the apertures are elliptical.

12. The bone fusion screw as recited in claim 1, wherein the head has an outer diameter that is greater than an outer diameter of the threads.

13. The bone fusion screw as recited in claim 1, wherein the head comprises structure configured for receiving a driver for rotating the body.

14. The bone fusion screw as recited in claim 1, wherein the channel is coaxial with the chamber forming a cannula through the bone fusion screw.

15. The bone fusion screw as recited in claim 1, wherein the outer surface of the body is roughened to assist in osteointegration.

16. A system for fixation of bone, comprising:

a bone fusion screw comprising:

a hollow elongated body having a longitudinal axis extending between a proximal end and an open distal tip, the body defining an inner chamber bounded by an inner surface of the body and extending between the proximal end and the distal tip, the body including threads formed along at least a portion of the outer surface;

a head portion integral with the body at the proximal end, wherein the head portion has internal threads within a channel;

at least one wedge-shaped tooth extending axially distally from the distal tip, the at least one tooth comprising a cutting edge for cutting bone to form a bore as the body is rotated; and an intermediate fluted portion adjacent the distal tip and intersecting the threads along the body, the fluted portion comprising at least one flute having a first end integral with the tooth at the distal tip for assisting removal of bone cuttings from said cutting edge;

wherein the body defines a plurality of apertures between the threads and opening into the chamber, and wherein pairs of opposed apertures are located at a plurality of spaced axial locations along the body for providing a see through opening through the body at each of the spaced axial locations; and a driver having a distal end that is engageable with the head for rotating the bone fusion screw; wherein at least a portion of the distal end portion of the driver has an external threaded surface configured to be threadably coupled with the internal threads to secure the driver within the channel.

17. The system for bone fixation as recited in claim 16, wherein the driver comprises a handle portion and a distal driving end portion that extends from the handle portion.

18. The system for bone fixation as recited in claim 17, wherein the distal end portion conforms to at least a portion of a channel formed in the body.

19. The system for bone fixation as recited in claim 16, further comprising a washer configured to be disposed around the body before implanting the screw.

20. The system for bone fixation as recited in claim 19, wherein the washer includes axial teeth extending from a distal surface.

21. A bone fusion screw, comprising:

a hollow elongated body having a longitudinal axis extending between a proximal end and an open distal tip, the body defining an inner chamber bounded by an inner surface of the body and extending between the proximal end and the distal tip, the body including threads formed along at least a portion of the outer surface;

a head integral with the proximal end of the body, the head defining a channel wherein the surface of the head defining the channel comprises threads adapted to be threadably coupled to a threaded driver to secure the driver within the channel of the head;

at least one wedge-shaped tooth extending axially distally from the distal tip, the at least one tooth comprising a cutting edge for cutting bone to form a bore in the bone as the body is rotated; and an intermediate fluted portion adjacent the distal tip and intersecting the threads along the body, the fluted portion comprising at least one flute having a first end integral with the tooth at the distal tip for assisting removal of bone cuttings from the cutting edge;

wherein the body defines a plurality of apertures between the threads and opening into the chamber, and wherein the surface of the head defining the channel comprises threads adapted to be threadably coupled to a threaded driver to secure the driver within the channel of the head.

22. The bone fusion screw as recited in claim 21, wherein a transverse cross-section of the chamber is substantially circular.

23. The bone fusion screw as recited in claim 21, wherein the threads extend substantially between the proximal end and the distal end of the outer surface of the body.

24. The bone fusion screw as recited in claim 21, wherein the at least one tooth tapers radially outwardly from the inner surface of the body to the cutting edge for directing bone into the chamber upon rotation of the body in bone.

25. The bone fusion screw as recited in claim 21, wherein the at least one tooth comprises two cutting edges.

26. The bone fusion screw as recited in claim 21, wherein the at least one flute extends along the outer surface of the body in a direction substantially parallel to the longitudinal axis.

27. The bone fusion screw as recited in claim 21, wherein the flute extends along a helical path from the first end to the second end.

28. The bone fusion screw as recited in claim 27, wherein the threads on the outer surface of the body are oriented at a pitch that is different from the pitch of the helical path of the flute.

29. The bone fusion screw as recited in claim 21, wherein the fluted portion comprises two pairs of opposed flutes.

30. The bone fusion screw as recited in claim 21, wherein the apertures are adapted to receive bone growth material.

31. The bone fusion screw as recited in claim 21, wherein the apertures are elliptical.

32. The bone fusion screw as recited in claim 21, wherein the channel is coaxial with the chamber forming a cannula through the bone fusion screw.

33. The bone fusion screw as recited in claim 21, wherein the outer surface of the body is roughened to assist in osteointegration.

34. A system for fixation of bone, comprising:
a bone fusion screw comprising:
a hollow elongated body having a longitudinal axis extending between a proximal end and an open distal tip, the body defining an inner chamber bounded by an inner surface of the body and extending between the proximal end and the distal tip, the body including threads formed along at least a portion of the outer surface, wherein the body defines a plurality of apertures opening into the chamber;
a head portion integral with the body at the proximal end, the head portion having internal threads within a channel;
at least one wedge-shaped tooth extending axially distally from the distal tip, the at least one tooth comprising a cutting edge for cutting bone to form a bore as the body is rotated; and
an intermediate fluted portion adjacent the distal tip and intersecting the threads along the body, the fluted portion comprising at least one flute having a first end integral with the tooth at the distal tip for assisting removal of bone cuttings from said cutting edge; and
a driver having a distal end, at least a portion of the distal end portion of the driver having an external threaded surface configured to be threadably coupled with the internal threads of the head portion to secure the driver within the channel for rotating the bone fusion screw with the driver.

* * * * *